United States Patent [19]
Lu

[11] Patent Number: 5,880,823
[45] Date of Patent: *Mar. 9, 1999

[54] METHOD AND APPARATUS FOR MEASURING ATOMIC VAPOR DENSITY IN DEPOSITION SYSTEMS

[76] Inventor: Chih-Shun Lu, Intelligent Sensor Technology, Inc. 1012-A Linda Vista Ave., Mountain View, Calif. 94043

[ * ] Notice: The terminal 14 months of this patent has been disclaimed.

[21] Appl. No.: 258,243

[22] Filed: Jun. 10, 1994

[51] Int. Cl.[6] .................................................. G01J 3/42
[52] U.S. Cl. ......................... 356/72; 356/319; 118/712; 118/715
[58] Field of Search .................................... 356/300, 311, 356/316, 319, 73, 72; 118/715, 712

[56] References Cited

U.S. PATENT DOCUMENTS 3,734,620  5/1973  Cade ......................................... 356/73

OTHER PUBLICATIONS

Ahearn, Optical Bridge for an Atomic Absorption Rate Monitor and Control System, IBM Technical Disclosure Bulletin. vol. 14, No. 1, Jun. 1971, pp. 148 and 149.

Primary Examiner—F. L Evans
Attorney, Agent, or Firm—William Green & Assoc.

[57] ABSTRACT

A device that eliminates the baseline instability of Atomic Absorption Spectroscopy monitors by utilizing a dual-source, dual-beam optical configuration. The source of one beam, the measuring beam, is light emission from a hollow cathode lamp which is used to determine the atomic vapor density by conventional atomic absorption principles. The second source, the calibration beam, is an emission which has negligible absorption by the atomic vapor, and passes through the same optical path as the measuring beam. For each light source, one beam passes through the processing chamber before its intensity is analyzed. The intensity of a second beam is determined near the light source to provide a reference signal for ratio measurement. Using conventional signal processing, the atomic vapor density, and thus the deposition rate, can be precisely determined despite changes in light source intensity, window transmission and optical alignment.

16 Claims, 5 Drawing Sheets

METHOD AND APPARATUS FOR MEASURING ATOMIC VAPOR DENSITY IN DEPOSITION SYSTEMS

BACKGROUND OF THE INVENTION

1. Field of the Invention

This invention relates generally to the precise measurement of atomic vapor density in the fabrication of materials and devices during deposition, and particularly to the control of deposition rate and composition using atomic absorption spectroscopy.

2. Brief Description of the Prior Art

The fabrication of certain materials and devices, such as semi-conductor lasers, requires the control of very low growth rates, often less than 0.1 nm/s with an accuracy of greater than 1%.

Quartz Crystal Microbalances are commonly used to determine the amount of deposited mass. However such devices cannot distinguish among different materials, and are sensitive to other factors, such as temperature and stress.

Electron Impact Emission Spectroscopy has been used to determine vapor flux density and thus deposition rates. Although this procedure can distinguish among different materials and is highly sensitive, its long-term stability and operational pressure range limits or excludes its use in some processes. For example, its limitation to high vacuum conditions (less than $10^{-4}$ mbar) prohibits its use in thin film fabrication processes such as sputtering and reactive evaporation.

Mass Spectroscopy methods are both material specific and highly sensitive, but are subject to the same limitations as Electron Impact Emission Spectroscopy.

Another drawback to the prior art methods and devices described above is that all require the presence of a sensor within the processing chamber. The location of a sensor within the processing chamber may disturb the process or contaminate the chamber. Additionally, sensors generally must be physically located in a different portion of the chamber than the location of the substrates where the actual film growth occurs. The difference between the substrate location and the sensor location may introduce errors in process control.

Atomic Absorption Spectroscopy is a promising technique for measuring vapor density. This technique is material specific, highly sensitive, and non-intrusive. It has been widely accepted as a standard tool for chemical analysis of elements. Atomic Absorption Spectroscopic devices, employ an optical system consisting of a special light source, a wavelength selection device and a photodetector. U.S. Pat. No. 3,654,109 discloses the basic concepts of such systems. Notwithstanding, the favorable characteristics of such devices, the photodetector has its maximum output at zero deposition rate, i.e., without the presence of vapor flux. This reference baseline at zero deposition rate can be affected by changes in the light source intensity, the optical system alignment and the transmission of optical windows. The signal changes brought about from these undesirable effects cannot be separated from the real absorption signal after the deposition process starts. The inability to separate these signal changes causes baseline instability and can significantly affect the accuracy and repeatability of vapor flux measurements.

OBJECTS AND ADVANTAGES OF THE INVENTION

It is the primary object of this invention to improve the control of deposition rates and compositions of complex films using atomic absorption spectroscopy.

A further object is to improve conventional Atomic Absorption Spectroscopy monitors by solving the problems caused by reference baseline instability. This object has the advantage of providing a material specific, highly sensitive and non-intrusive system for monitoring and controlling deposition processes.

A further object is the measurement of deposited materials within a wide range of operational pressures without requiring vacuum conditions. This permits the use of the invention in thin film fabrication processes such as sputtering and reactive evaporation.

Another object is a device in which the sensor is located outside of the processing chamber. This eliminates the effect of the intrusion of the sensor into the process and also eliminates errors caused by the location of the sensor and substrate in different places within the chamber.

SUMMARY OF THE INVENTION

This invention provides a device that eliminates the baseline instability of Atomic Absorption Spectroscopy monitors by utilizing a dual-source, dual-beam optical configuration. The source of one beam, the measuring beam, is light emission from a hollow cathode lamp which is used to determine the atomic vapor density by conventional atomic absorption principles. The second source, the calibration beam, is an emission which has negligible absorption by the atomic vapor, and passes through the same optical path as the measuring beam. For each light source, one beam passes through the processing chamber before its intensity is analyzed. The intensity of a second beam is determined near the light source to provide a reference signal for ratio measurement. Using conventional signal processing, the atomic vapor density, and thus the deposition rate, can be precisely determined despite changes in light source intensity, window transmission and optical alignment.

DETAILED DESCRIPTION OF THE INVENTION

Description of the Device

Figure 1:
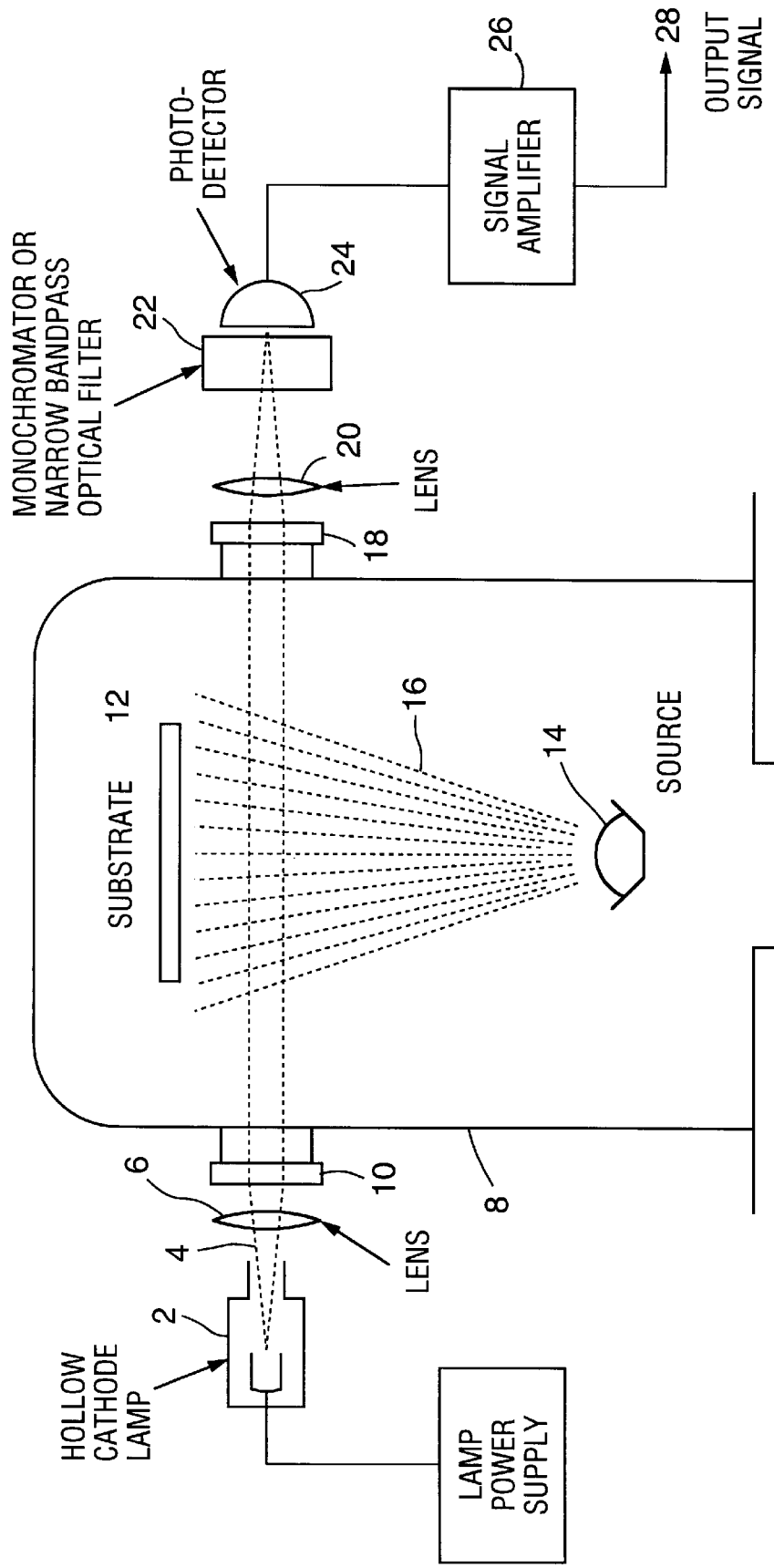
FIG. 1 illustrates a typical single-beam optical configuration of conventional Atomic Absorption Spectroscopy, hereinafter "AAS" Monitors.

FIG. 1 illustrates a typical single-beam optical configuration of a conventional Atomic Absorption Spectroscopy Monitor. The optical system consists of a special light source, a wavelength selection device and a photodetector. The light source 2 is typically a hollow cathode lamp (HCL) with its cathode made of the same material as the vapor flux to be measured. The HCL, when energized, emits the characteristic radiation of the cathode material. The radiation 4 is passed through lens 6 and directed into deposition chamber 8 through entrance window 10. Deposition chamber 8 contains substrate 12, supported in a conventional manner, and a vapor source 14. Vapor source 14 generates the atomic vapor flux 16 which is deposited upon substrate 12. When radiation 4 is allowed to pass through the atomic vapor flux 16 within deposition chamber 8, absorption takes place along its passage. The amount of absorption then becomes a measure of the vapor flux density which determined the film growth rate. Radiation 4 exits chamber 8 through exit window 18 and is directed through exit lens 20 to a wavelength selection device 22, which can be either a monochromator or a narrow bandpass optical filter and is used to reject undesirable radiation from the ambient and the HCL. Photodetector 24 measures the emission intensity after absorption and the resultant signal is amplified by signal amplifier 26 to produce an output signal 28 which is a function of the rate of deposition and can be analyzed to produce a film thickness measurement. To further discriminate the ambient radiation, the light source is often modulated, either electronically or mechanically, so that a phase sensitive signal detection scheme can be used.

A major problem associated with the single-beam optical configuration, such as disclosed in the Hohl et al patent, is the baseline instability. Unlike most deposition monitors, the photodetector of an AAS monitor has its maximum output at zero deposition rate, i.e., without the presence of vapor flux. Unfortunately, this reference baseline at zero deposition rate can be affected by changes in the light source intensity, the optical system alignment and the transmission of optical windows. The signal changes brought about from these undesirable effects cannot be separated from the real absorption signal after the deposition process gets started. This can significantly affect the accuracy and repeatability of vapor flux measurements. Several methods have been tried to improve the baseline stability of AAS monitors, such as periodic calibration of baseline by blocking off the vapor flux from the sampled region [Klausmeier-Brown et al, Appl. Phys. Lett. 60, 657 (1992)], ratio measurement of HCL intensities before and after absorption [Benerofe et al, Proc. North American MBE Conf. (Stanford, California) 1993] and the addition of a local feedback loop to stabilize the HCL [Chalmers and Killeen, Appl. Phys. Lett. 63, 3131 (1993)]. These methods of improvement have rather limited utility because blocking off the vapor flux is not permitted in real-time deposition rate control, and eliminating the problem of light source intensity changes still leaves the effect of window coating unresolved. Thus despite the many attractive features of the AAS technique, it has never been accepted as a practical tool for precise control of thin film growth rate.

This invention is specifically directed to a method for eliminating the baseline instability associated with AAS monitors so that the full advantages of AAS techniques can be realized for precise control of thin film growth rate over extended periods. The method utilizes a new optical configuration which can be readily fitted to a vacuum deposition chamber. An appropriate signal processing technique is then implemented to separate the signal change due to optical system transmission changes from that due to absorption by the atomic vapor flux. Changes in light source intensity, optical alignment and window transmission will not affect the zero deposition rate baseline. Thus the full advantages of AAS techniques for determining vapor flux density can be realized.

Figure 2:
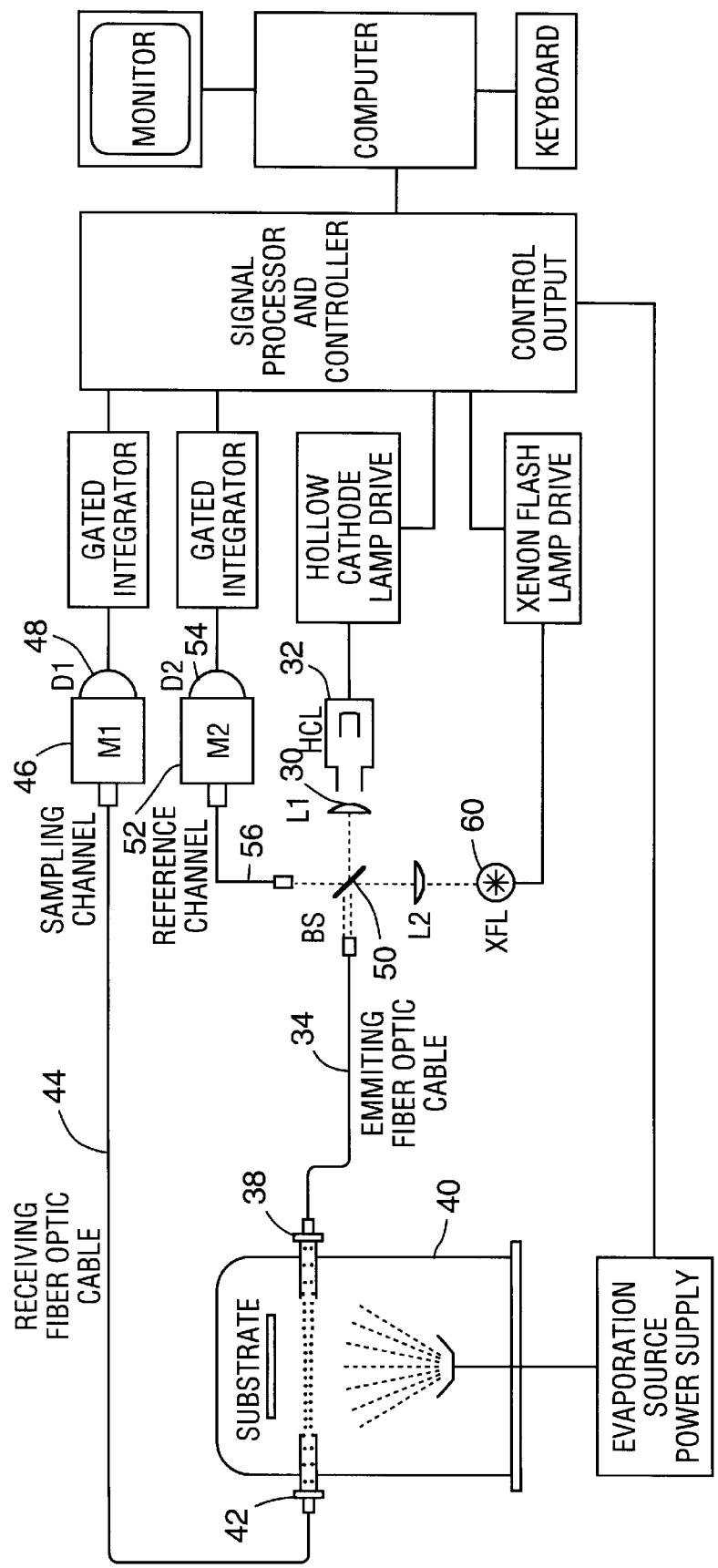
FIG. 2 illustrates the dual-source dual-beam optical configuration of this invention.

FIG. 2 illustrates the dual-source, dual-beam optical configuration of this invention. Light 30 is generated from a hollow cathode lamp (HCL) 32 focused onto the end of a fiber optic cable 34 by a lens 36. Emitting fiber optic cable 34 guides light 30 to an emitting probe 38 which is attached externally to a properly located optical window on deposition chamber 40. On the opposite side of deposition chamber 40, a receiving probe 42 collects the light and sends it back to sampling channel monochromator 46 through receiving fiber optic cable 44. Monochromator 46 is used to isolate the desired specific atomic emission line from the HCL emission and its intensity is measured with a sampling channel silicon photodetector 48. This optical train alone forms a conventional single-beam atomic absorption monitor.

The problems associated with intensity changes in the light source are solved by the addition of a reference signal channel. As shown in FIG. 2, a reference signal is established by using a beam splitter 50 to direct a portion of the light from the hollow cathode lamp 32 to a second photodetection system consisting of reference channel monochrometer 52 and reference channel silicon photodector 54 via a short section of fiber optic cable 56.

The configuration as described thus far does not solve the problem of transmission changes due to window coating and shifting optical alignment. In many applications a conventional double-beam optical configuration can solve this problem, but its implementation in typical vacuum deposition chambers is extremely difficult. The method of this invention solves this problem by adding a second light source in a manner so that its emission is practically not absorbed by the atomic vapor.

As shown in FIG. 2., a xenon flash lamp 60, chosen for its high-intensity emission over a broad spectral range is provided. Except for a short path between the beam splitter and each light source, light from xenon flash lamp 60, the calibration beam, travels through the same optical path as that from the hollow cathode lamp 32. Of the broad emission spectrum from the xenon flash lamp, only a narrow band of emission is allowed to reach the photodetector due to the limited bandwidth of the monochromator, about 5 nm in the present case. However, this "narrow" bandwidth is still several orders of magnitude broader than any absorption linewidth, which is typically on the order of $10^{-3}$ nm. Consequently, this selected band of emission from the xenon flash lamp suffers only negligible attenuation after passing through the atomic vapor flux. Furthermore, the center wavelength of the selected emission band is automatically tuned to that of the atomic emission line because of the monochromator setting. Thus the spectral response of the optical train is taken into consideration as well. When the duty cycles of the two light sources are properly controlled by a timing circuit, the absorption by the vapor flux alone can be obtained through a straightforward analysis of the photodetector outputs. The absorption A by the atomic vapor flux is given by $$A=1-\{[D1(1)-D1(0)]/[D2(1)-D2(0)]\}/\{[D1(2)-D1(0)]/[D2(2)-D2(0)]\}, \quad (1)$$

where $D1(x)$ and $D2(x)$ denote, respectively, the output of detector D1 (sampling channel) and D2 (reference channel) in lamp state $x$ [$x=0$ for HCL and XFL both off (background signal); $x=1$ for XFL off only; $x=2$ for HCL off only]. The absorption value thus obtained is unaffected by any changes in the entire optical system other than the absorption by the vapor flux.

Figure 3:
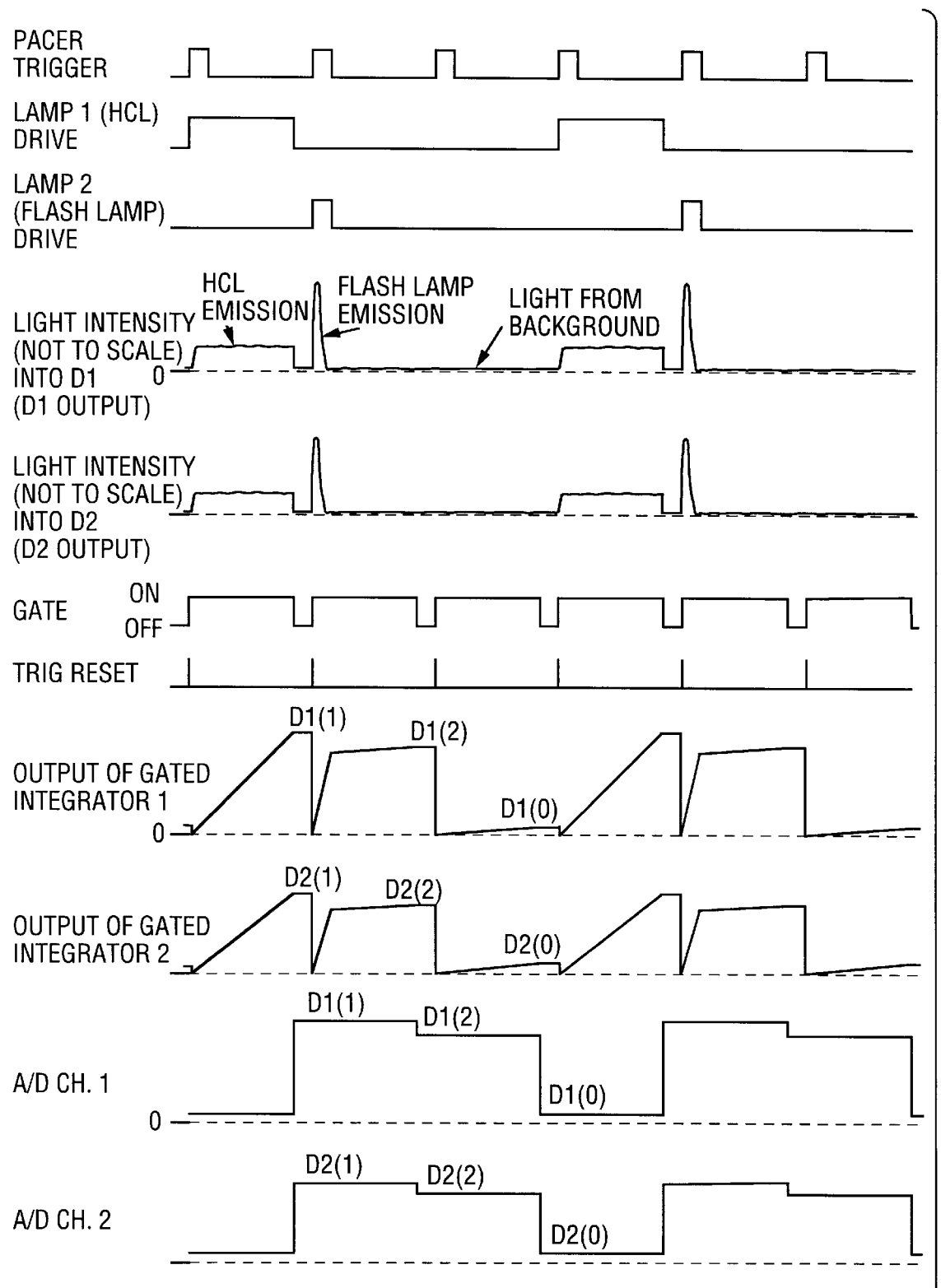
FIG. 3 is a timing diagram for light sources and photo-detection circuits.

FIG. 3 shows a typical timing diagram. In actual implementation, the sampling frequency of the hollow cathode lamp needs not to be the same as that of the Xenon Flash lamp. The intensity measurements can be averaged for a selected number of samples to improve the signal-to-noise ratio.

Figure 4:
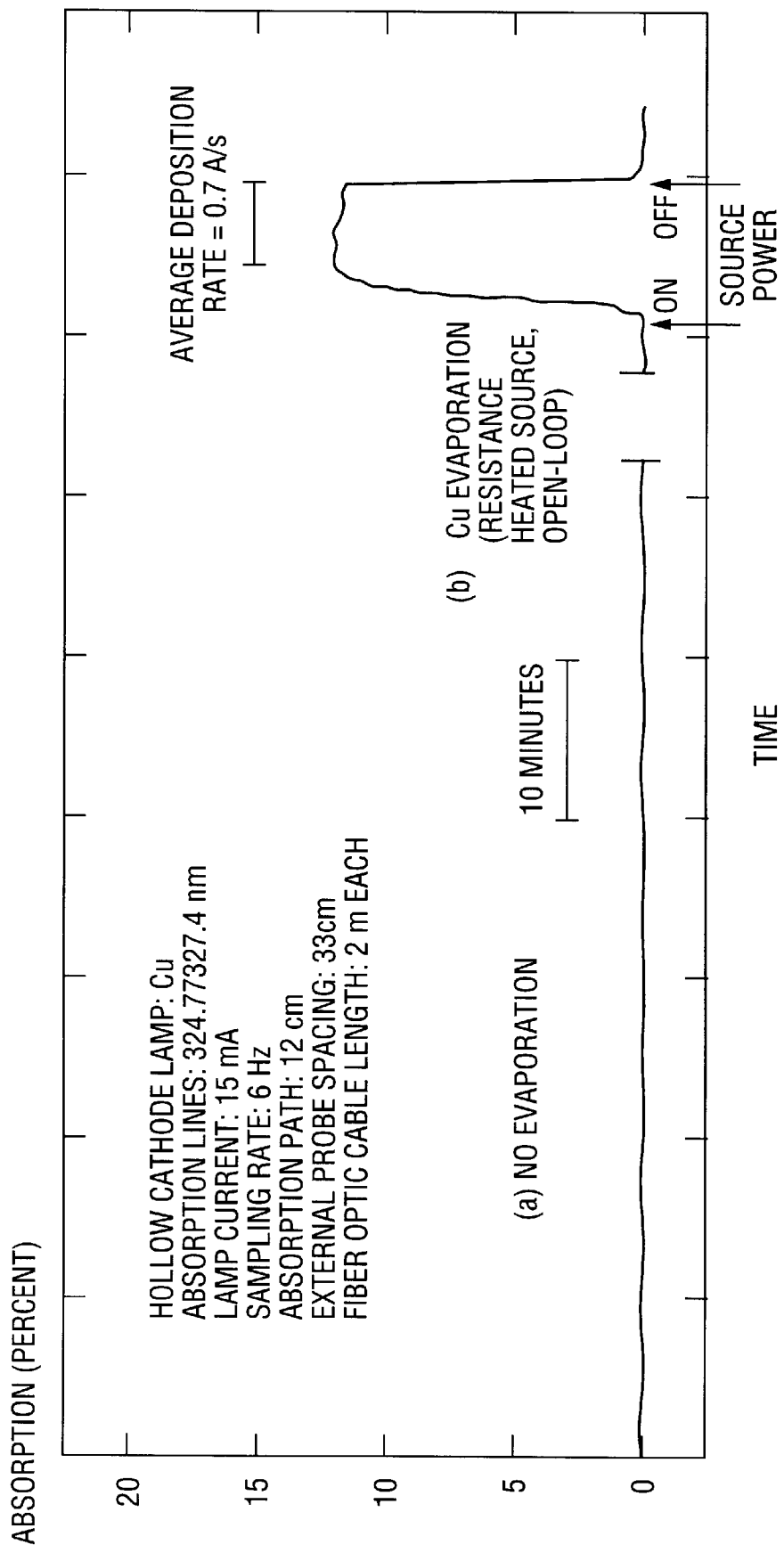
FIG. 4 is a chart plotting time versus absorption in a Cu deposition.

FIG. 4 illustrates the results of an example in which a Cu HCL was operated at 10 mA with on/off frequency of 6 Hz.

The XFL was operated at half the frequency, 3 Hz. The Cu emission lines at 324.7 and 327.4 nm were selected for absorption measurements. An emission band approximately 5 nm wide and centered at about 326 nm was selected from the XFL emission for optical system transmission calibration. A dual-channel monochromator was used to select the said emissions from both HCL and XFL light sources. Standard gated integration technique was employed for photo-signal detection by silicon photodetectors. A conventional electronic unit was used to control the timing of each lamp and to perform signal processing. An analog control signal was available from this unit for closed-loop control of the deposition source, but was not used in this experiment. A personal computer was used for data display and programming. Since the HCL intensity and optical system transmission changes are typically slow, D2(1), D2(0), D1(2), D1(0), D2(2) and D2(0) in Equation 1 were averaged over 160 samples to improve the signal-to-noise ratio of A. D1(1) and D1(0) were not averaged so that the value of A was updated at the same rate as the HCL chopping frequency, i.e. 6 Hz for this example. The fast update for A, which determines the deposition rate, is desirable for real-time closed-loop control of deposition source. The Cu deposition was carried out in a vacuum system using a resistance heated source. The baseline for absorption measurement with no vapor flux was stable to within ±0.1% over 1 hour. With a 12 cm absorption pathlength, a signal-to-noise ratio of better than 100 was obtained for a Cu deposition rate of 0.07 nm/s, as calibrated by a quartz crystal microbalance. The results indicated that, for Cu deposition, this method can detect a deposition rate as low as 0.01 nm/s and maintain its accuracy over an extended time period. With a longer absorption pathlength and/or a substrate-to-source distance, the sensitivity of this method can be further increased.

Figure 5:
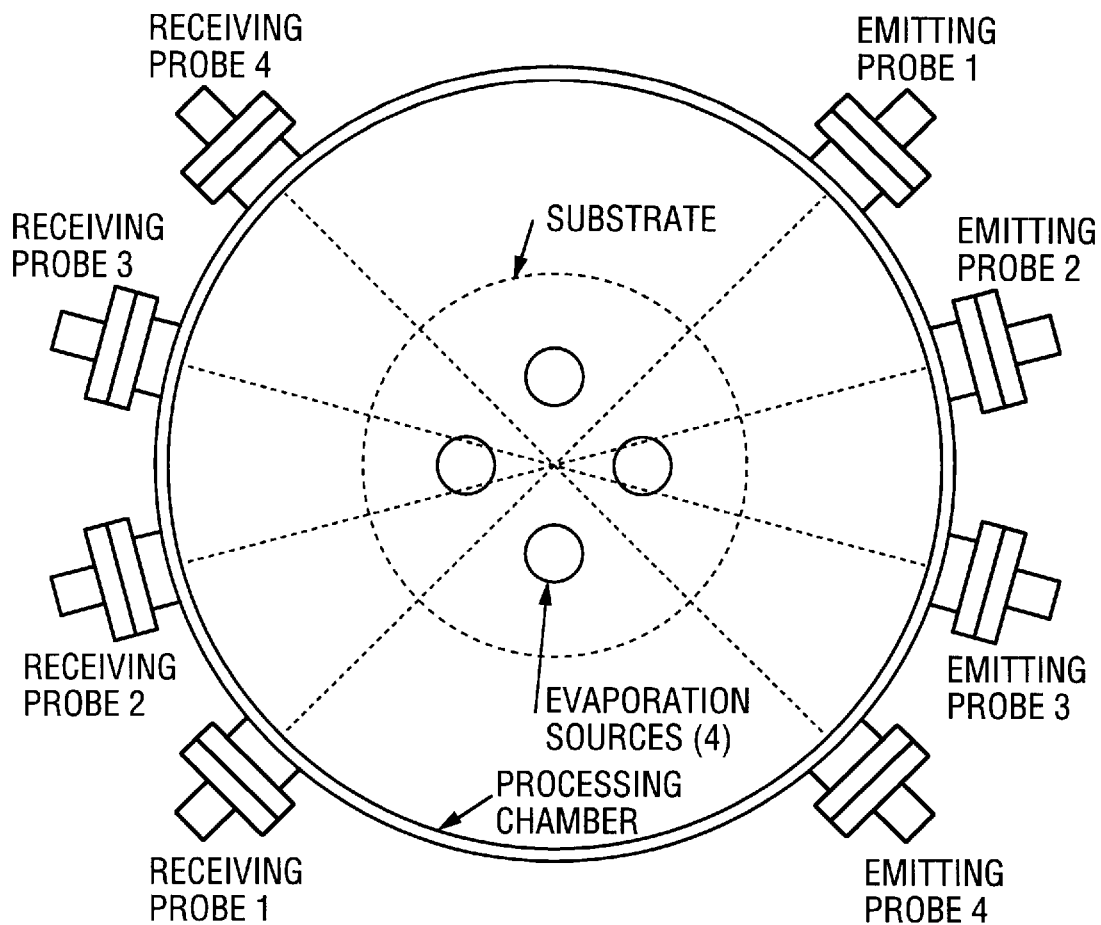
FIG. 5 illustrates a device for controlling film composition during a co-deposition process with four different sources.

In addition to thermal evaporation processes, the AAS monitor as described herein is also useful in controlling film growth rate in reactive and non-reactive sputtering, ion plating, ion beam sputtering, laser ablation reactive evaporation and certain chemical vapor deposition processes. Because there is no pressure limitation to the AAS technique, it is also applicable to non-vacuum processes to measure atomic vapor density. By selecting an emission line from an ionic species in an appropriate light source, the density of an ionic species in free state can be determined. Such applications include the monitoring of ion beam current in ion milling, plasma etching and ion implantation processes. Because an AAS monitor designed for detecting one particular atomic species (by using an HCL of the specific element) does not respond to the presence of any other species of atoms or molecules, precise film composition control in multi-source co-evaporation or co-sputtering processes can be achieved with the use of multiple units of AAS monitor in a typical setup as shown in FIG. 5.

Modifications can be made to the invention as illustrated in the preferred embodiment of FIG. 2, without departing from the scope of the invention. For example, the hollow cathode lamp can be replaced by other light sources, which generate characteristic atomic emissions, such as electrodeless discharge lamps, and tunable lasers. Instead of turning the light sources on and off electrically as illustrated herein, their intensities can be modulated by using mechanical light choppers or other means. Other synchronous or phase sensitive signal detection techniques can be used to replace the gated integration method used in the example. Narrow bandpass optical filters or other wavelength selection devices can be substituted for the monochromators used in this embodiment for wavelength filters. The silicon photodetectors used as disclosed herein are convenient and relatively inexpensive, but other types of photoconductors, such as photomultipliers, can be used in place of silicon photodetectors. The fiber optic cables between the AAS monitor and the deposition chamber are a convenient medium for transmitting signals. The fiber optic cables can also be extended into the processing chamber through fiber optic feedthrough so that a pair of appropriately located windows on the processing chamber would no longer be required. The method of this invention could also be implemented at the windows of a deposition chamber without the need for fiber optical cables.

The invention as described herein is an improved system and method for controlling the deposition rate and composition of complex films using atomic absorption spectroscopy. It solves the problem of reference baseline instability inherent in atomic absorption spectroscopy by an optical scheme that allows a calibration light beam from a second source to pass through the same passage as the measuring light beam, i.e. emission from the HCL source. The intensity of the calibration light beam suffers only a negligible amount, and thus can be considered as unaffected, by the vapor flux. The center wavelength of this calibration light coincides with that of the selected atomic emission line. Therefore, the spectral response of the optical system (except the vapor flux) affects both calibration and measuring beams to the same degree in terms of signal attenuation. In the preferred embodiment, a high-intensity, broad-band xenon lamp in pulsed mode is used as the calibration light source. With proper on/off sequence of each lamp and synchronous photo-signal detection technique, the true absorption due to atomic vapor flux can be precisely determined independently of any transmission changes in the optical system, including the transmission changes due to optical window coating during typical deposition processes over extended time periods.

The preferred embodiment and variations disclosed herein are not intended to limit the scope of the invention, as it will be apparent to those skilled in the art that the embodiments described may be modified without departing from the spirit and scope of the invention, as defined in the following claims:

I claim:

1. In an atomic absorption spectroscopy system for measuring and controlling the deposition rate and composition of vapor deposited films upon a substrate, comprising a source for generating a light beam including a selected wavelength that can be absorbed by a specie to be deposited, the measuring beam, position to direct said measuring beam along a sampling channel, through the vapor in a deposition chamber; and a photodetection system for determining the rate of deposition by measuring the amount of light absorbed at the selected wavelength the improvement comprising:

(a) a second light source for generating a light beam, the calibration beam, having a bandwidth substantially broader than the absorption linewidth of the specie to be deposited, but a center wavelength the same as that of the absorption line of the specie to be deposited, positioned to direct light substantially along the same optical path as the measuring beam, the sampling channel;

(b) means for measuring the amount of light absorbed from the calibration beam at pre-determined on-off duty cycles;

(c) means for determining the absorption by the vapor unaffected by changes in optical components of the system by comparing an output representative of the measuring beam transmitted along the sampling channel with an output representative of the calibration beam transmitted along the sampling channel under conditions where both sources are off and one source is off.

2. The apparatus of claim 1 wherein said second light source is a Xenon flash lamp.

3. The apparatus of claim 1 additionally comprising (d) means for creating a reference signal by splitting a portion of the light from each of said sources (e) a second photodetection system having an optical path that does not pass through the deposition chamber, the reference channel;

(f) means for directing said reference signal along said reference channel; and (g) means for comparing the light collected from the sampling channel to the light collected from the reference channel;

whereby measurements may be adjusted for inaccuracies associated with intensity changes in the light sources.

4. The apparatus of claim 1 in which the measuring beam light source is a hollow cathode lamp.

5. The apparatus of claim 1 in which fiber-optic cables are used to transmit light along the sampling channel.

6. The apparatus of claim 3 in which fiber-optic cables are used to transmit light along the sampling and reference channels.

7. The apparatus of claim 3 in which fiber-optic cables are used to transmit light along the sampling channel.

8. The apparatus of claim 3 in which fiber-optic cables are used to transmit light along the reference channel.

9. In an atomic absorption spectroscopy method for measuring and controlling the deposition rate and composition of vapor deposited films upon a substrate, by generating a light beam having a selected wavelength that can be absorbed by a specie to be deposited to form a measuring beam, directing said measuring beam along a sampling channel, through the vapor in a deposition chamber; and determining the rate of deposition by measuring the amount of light absorbed at the selected wavelength using a photodetection system, the improvement comprising:

(a) directing a beam from a second light source, the calibration beam, having a bandwidth substantially broader than the absorption linewidth of the specie to be deposited, but a center wavelength the same as that of the absorption line of the specie to be deposited, substantially along the same optical path as the measuring beam, the sampling channel;

(b) measuring the amount of light absorbed from the calibration beam at pre-determined on-off cycles;

(c) determining the absorption by the vapor by comparing an output representative of the measuring beam transmitted along the sampling channel with an output representative of the calibration beam transmitted along the sampling channel under conditions where both sources are off and one source is off.

10. The method of claim 9 additionally comprising (d) creating a reference signal by splitting a portion of the light from each of said sources and directing said portions to a second photodetection system along an optical path that does not pass through the deposition chamber, the reference channel; and (e) comparing the light collected from the sampling channel to the light collected from the reference channel;

whereby measurements may be adjusted for inaccuracies associated with intensity changes in the light sources.

11. The method of claim 9 in which the measuring beam light source is a hollow cathode lamp.

12. The method of claim 9 in which the calibration beam light source is a Xenon flash lamp.

13. The method of claim 10 in which light is transmitted along the sampling channel by fiber-optic cables.

14. The method of claim 10 in which the light is transmitted along the reference channel by fiber-optic cables.

15. The method of claim 10 wherein the light is transmitted along the sampling and reference channels by fiber-optic cables.

16. The method of claim 9 in which the light is transmitted along the sampling channel by fiber-optic cables.

* * * * *